(12) United States Patent
Clarner et al.

(10) Patent No.: US 10,010,142 B2
(45) Date of Patent: Jul. 3, 2018

(54) LOOP FASTENING MATERIAL

(71) Applicant: VELCRO BVBA, Deinze (BE)

(72) Inventors: Mark A. Clarner, Manchester, NH (US); Christopher M. Gallant, Nottingham, NH (US)

(73) Assignee: Velcro BVBA (BE)

( * ) Notice: Subject to any disclaimer, the term of this patent is extended or adjusted under 35 U.S.C. 154(b) by 418 days.

(21) Appl. No.: 14/725,420

(22) Filed: May 29, 2015

(65) Prior Publication Data

US 2016/0345686 A1 Dec. 1, 2016

(51) Int. Cl.
| | |
|---|---|
| *A44B 18/00* | (2006.01) |
| *A61F 13/62* | (2006.01) |
| *B32B 5/06* | (2006.01) |
| *D04H 11/08* | (2006.01) |
| *B32B 5/02* | (2006.01) |
| *B32B 5/08* | (2006.01) |
| *B32B 5/26* | (2006.01) |
| *B32B 7/12* | (2006.01) |
| *B32B 27/12* | (2006.01) |
| *B32B 27/32* | (2006.01) |
| *B32B 29/02* | (2006.01) |
| *B32B 3/30* | (2006.01) |
| *D04H 3/105* | (2012.01) |

(52) U.S. Cl.
CPC ........ *A44B 18/0011* (2013.01); *A61F 13/627* (2013.01); *B32B 3/30* (2013.01); *B32B 5/02* (2013.01); *B32B 5/06* (2013.01); *B32B 5/08* (2013.01); *B32B 5/26* (2013.01); *B32B 7/12* (2013.01); *B32B 27/12* (2013.01); *B32B 27/32* (2013.01); *B32B 29/02* (2013.01); *D04H 3/105* (2013.01); *D04H 11/08* (2013.01); *B32B 2262/02* (2013.01); *B32B 2262/12* (2013.01); *B32B 2262/14* (2013.01); *B32B 2307/542* (2013.01); *B32B 2307/718* (2013.01); *B32B 2307/7242* (2013.01); *B32B 2307/734* (2013.01); *B32B 2435/00* (2013.01)

(58) Field of Classification Search
None
See application file for complete search history.

(56) References Cited

U.S. PATENT DOCUMENTS

| | | |
|---|---|---|
| 2,706,324 A | 4/1955 | Cogovan |
| 3,950,587 A | 4/1976 | Colijn et al. |
| 4,010,302 A | 3/1977 | Anderson et al. |

(Continued)

FOREIGN PATENT DOCUMENTS

| | | |
|---|---|---|
| DE | 3006805 | 9/1981 |
| EP | 211564 | 2/1992 |

(Continued)

OTHER PUBLICATIONS

U.S. Appl. No. 14/725,463, filed May 29, 2015, Gallant et al.

(Continued)

*Primary Examiner* — David Sample
*Assistant Examiner* — Nicole T Gugliotta
(74) *Attorney, Agent, or Firm* — Fish & Richardson P.C.

(57) ABSTRACT

A touch fastener loop material has a non-woven web of fibers forming both a base and a field of high-tenacity hook-engageable loops extending outward from one broad side of the base. The fibers are distributed such that the field of loops has a particular fiber volume distribution as a function of elevation above the base.

18 Claims, 6 Drawing Sheets

(56) References Cited

U.S. PATENT DOCUMENTS

| | | |
|---|---|---|
| 4,154,889 A | 5/1979 | Platt |
| 4,258,094 A | 3/1981 | Benedyk |
| 4,324,824 A | 4/1982 | Narens et al. |
| 4,379,189 A | 4/1983 | Platt |
| 4,439,476 A | 3/1984 | Guild |
| 5,216,790 A | 6/1993 | Eschenbach |
| 5,265,954 A | 11/1993 | Keil |
| 5,630,896 A | 5/1997 | Corbin et al. |
| 5,891,547 A | 4/1999 | Lawless |
| 6,086,984 A | 7/2000 | DiMaggio et al. |
| 6,329,016 B1 | 12/2001 | Shepard et al. |
| 6,642,160 B1 | 11/2003 | Takahashi |
| 6,783,834 B2 | 8/2004 | Shepard et al. |
| 6,893,525 B1 | 5/2005 | Schmidt et al. |
| 7,117,571 B2 | 10/2006 | Dilo |
| 7,156,937 B2 | 1/2007 | Provost et al. |
| 7,465,366 B2 | 12/2008 | Provost et al. |
| 7,547,469 B2 | 6/2009 | Provost et al. |
| 7,562,426 B2 | 7/2009 | Barker et al. |
| 8,500,940 B2 | 8/2013 | Shepard et al. |
| 8,673,097 B2 | 3/2014 | Barker et al. |
| 8,753,459 B2 | 6/2014 | Provost et al. |
| 2002/0160143 A1 | 10/2002 | Shepard et al. |
| 2004/0157036 A1 | 8/2004 | Provost et al. |
| 2005/0196581 A1 | 9/2005 | Provost et al. |
| 2005/0196583 A1 | 9/2005 | Provost et al. |
| 2005/0208259 A1 | 9/2005 | Provost et al. |
| 2005/0217092 A1 | 10/2005 | Barker et al. |
| 2006/0225258 A1 | 10/2006 | Barker et al. |
| 2007/0178273 A1 | 8/2007 | Provost et al. |
| 2008/0113152 A1 | 5/2008 | Provost et al. |
| 2011/0253289 A1 | 10/2011 | Shepard |
| 2013/0052399 A1 | 2/2013 | Barker |
| 2013/0052403 A1 | 2/2013 | Barker et al. |
| 2016/0222559 A1 | 8/2016 | Gallant et al. |

FOREIGN PATENT DOCUMENTS

| | | |
|---|---|---|
| EP | 0780505 | 1/2003 |
| EP | 1276348 | 1/2003 |
| EP | 1279348 | 1/2003 |
| GB | 1228431 | 4/1971 |
| JP | 7171011 | 7/1995 |
| JP | 09317 | 1/1997 |
| WO | WO 2001080680 | 11/2001 |
| WO | WO 2016/192907 | 12/2016 |

OTHER PUBLICATIONS

Non-Final Office Action in U.S. Appl. No. 14/725,463, dated Dec. 28, 2016, 16 pages.

International Search Report and Written Opinion in International Application No. PCT/EP2016/051911, dated May 13, 2016, 11 pages.

International Search Report and Written Opinion in International Application No. PCT/EP2016/059377, dated Aug. 1, 2016, 11 pages.

International Search Report and Written Opinion in International Application No. PCT/EP2016/059380, dated Aug. 1, 2016, 11 pages.

U.S. Appl. No. 14/725,463, filed May 29, 2015.

Written Opinion in International Application No. PCT/EP2015/059377, dated May 8, 2017, 8 pages.

FIG.9

LOOP FASTENING MATERIAL

TECHNICAL FIELD

This invention relates to fibrous materials having a fastening surface from which hook-engageable loops extend.

BACKGROUND

Touch fasteners are particularly desirable as fastening systems for lightweight, disposable garments, such as diapers. In an effort to provide a cost-effective loop material, some have recommended various alternatives to weaving or knitting, such as by needling a lightweight layer of fibers to form a light, non-woven material that can then be stretched to achieve even lighter basis weight and cost efficiency, with the loop structures anchored by various binding methods, and subsequently adhered to a substrate. U.S. Pat. No. 6,329,016 teaches one such method, for example.

Materials with lower unit costs and better performance are desired. Reducing fiber content can lower cost, but can also affect overall performance or load-carrying capacity of the loop material, as well as the dimensional stability and handling efficiency of the loop product. Also, choice of fiber material is often compromised by a need for the loop material to be weld-compatible with a substrate (e.g., an outer layer of a diaper) to which the loop material is to be permanently bonded, and by the load-bearing requirements of the fastener loop fibers.

Various methods of bonding fibers to underlying substrates have also been taught, for forming touch fasteners and other loop-bearing materials.

SUMMARY

Various aspects of the invention feature a hook-engageable fastener loop material having a particular combination of characteristics of a product property that we call Fiber Volumetric Ratio. In particular, we believe that manufacturing a fastener loop material to have a maximum Fiber Volumetric Ratio (MFVR, as defined herein) within a particular numeric range, while controlling where the MFVR occurs with respect to the distribution of Fiber Volumetric Ratio over the thickness of the product, can provide for a particularly cost-efficient engageability for many fastening applications.

We have found, for example, that loop materials having tenacious loops and fashioned to have an MFVR of between 5 and 25 percent, with the MFVR occurring closer to a Rising 5% Ratio Elevation than to a Falling 5% Ratio Elevation (as defined herein), can result in materials that have loop fields that are highly engageable for their weight.

We have also identified a particular characteristic that we call Critical Fiber Volume Percentage (CFVP), and have determined that CFVP, which we believe has not been previously appreciated, is a useful measure of a property that can provide particular value in many fastening applications if maintained below a certain level.

We have found, for example, that loop materials fashioned to have a CFVP of less than 60 percent, or between 60 percent and 20 percent, can provide a particularly useful set of performance characteristics as well as exceptional value, particularly when combined with the MFVR characteristics discussed herein. This can enable the commercial success of even more fastening applications, particularly disposable and single-use applications.

Because we appear to be the first to realize the significance of these loop material characteristics, we provide below a clear test to determine the MFVR and CFVP of a loop material.

One aspect of the invention features a touch fastener loop material with or of a non-woven web of fibers forming both a base and a field of hook-engageable loops of a tenacity of at least 1.1 grams per denier extending outward from one broad side of the base. The fibers are specifically distributed such that the field of loops has a Maximum Fiber Volumetric Ratio of between 5 and 25 percent, and the Maximum Fiber Volumetric Ratio occurs closer to the Rising 5% Ratio Elevation than to the Falling 5% Ratio Elevation.

In some examples, the touch fastener loop material also has a Critical Fiber Volume Percentage of between 20 and 60 percent.

For some applications, the Maximum Fiber Volumetric Ratio is between 8 and 20 percent, or between 10 and 15 percent.

In some cases, the tenacity is at least 5 grams per denier, and for some fastening applications the tenacity is at least 8 grams per denier.

The touch fastener loop material is preferably constructed to exhibit a Peel Strength of at least 500 grams force per inch width when mated with an HTH725 hook and tested according to ASTM D5170-98, and/or a Shear Strength of at least 8,000 grams force per square inch when mated with an HTH725 hook and tested according to ASTM D5169-98.

The touch fastener loop material can be constructed to be particularly air-permeable for applications requiring breathability. Some such examples exhibit a Frazier air permeability of at least 500 feet$^3$/feet$^2$/sec (150 m$^3$/m$^2$/sec).

In many cases the touch fastener loop material has an overall thickness, determined as prescribed below, of less than about 1.5 millimeters, such as between 1.0 and 1.5 mm.

For many fastening applications, such as those relating to disposable or single-use products, the web has an overall basis weight of between 20 gsm and 70 gsm.

The fibers can include, or even consist essentially of, multicomponent fibers such as bicomponent fibers having a sheath of a lower melting temperature than a core within the sheath. In such cases the fibers may be bonded within the base by resin of the sheath.

In some examples, the touch fastener loop material consists essentially of the non-woven web of fibers, bonded together by fused material of the fibers.

Preferably, the Maximum Fiber Volumetric Ratio occurs within a lower 30 percent of an elevation span between the Rising 5% Ratio Elevation and the Falling 5% Ratio Elevation.

The touch fastener loop material can be fashioned such that the base is dimensionally stable, meaning that it is of sufficient strength to be processed as a web without tearing or excessive elongation, at least to the point of being either laminated to another material or rolled for transportation. In some cases a touch fastener is formed by bonding a backing across a surface of the base opposite the field of loops, such as by an adhesive lamination technique. In some cases the loop material is laminated to an air-impermeable backing, such that the resulting product can be manipulated by suction.

As will be understood by those skilled in this art, the MFVR and CFVP of a fibrous loop material are each, in different senses, related to efficiency of the use of fibers in the loop material. MFVR can be said to be related to the peak density of material that a mate fastener element may encounter as in penetrates the working part of the field of loops, CFVP, on the other hand, can be said to be related to the proportion of the fiber mass of the material that is within the volume of the material accessible to engagement by hooks. While these over-generalizations should not be taken as a strict definition of either characteristic, they will help to explain why we believe that these characteristics are useful and significant parameters for further study and development in the advance of fastening science. Furthermore, samples exhibiting MFVR and/or CFVP in the ranges discussed herein have demonstrated very good flexibility and softness, while having web strengths suitable for processing and reliable attachment to various product surfaces.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
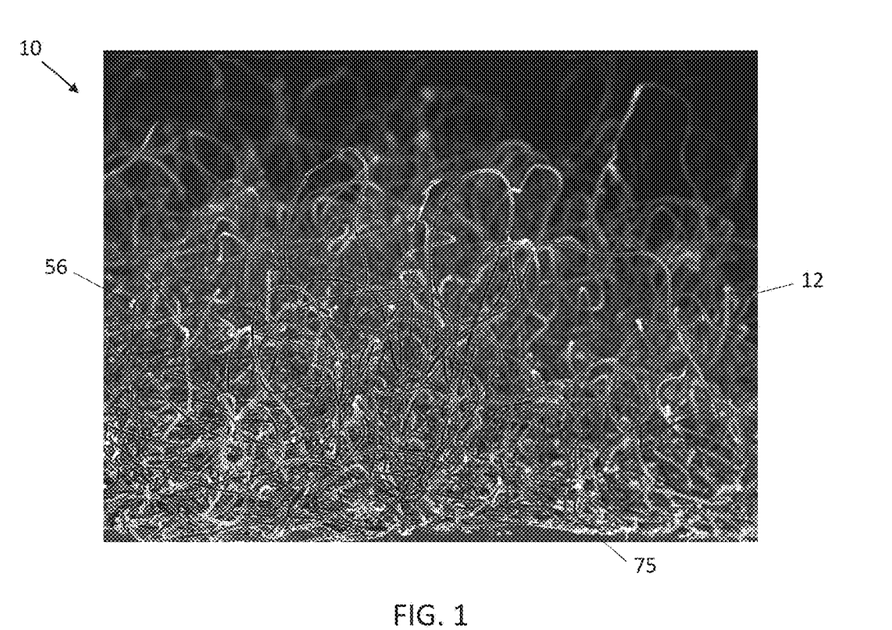
FIGS. 1 and 2 are enlarged photographic side views of a loop product.
Figure 2:
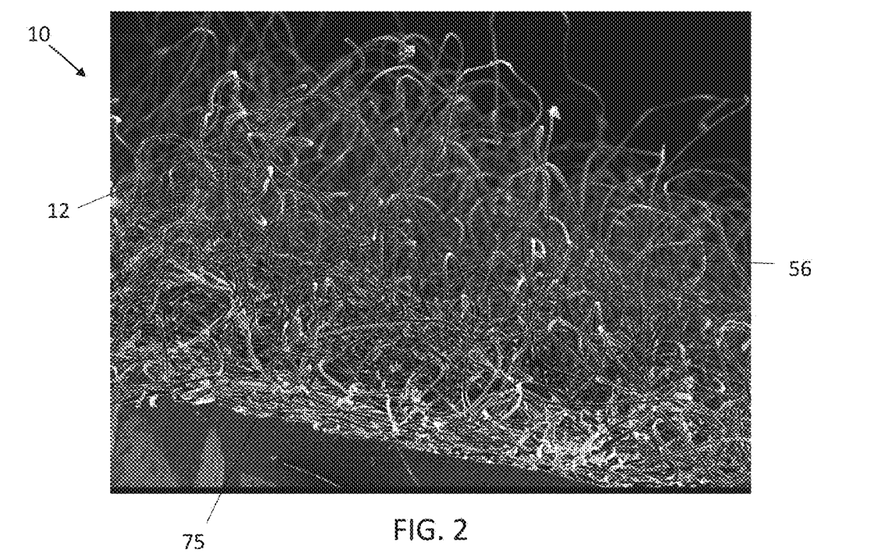

FIGS. 1 and 2 illustrate a loop material 10 having fibers 12 that form both a web 75 of fused fibers and a field of loops 56 extending from the web. These views are taken toward an edge of the loop product and centered about a particular loop structure for increased visibility of both the upstanding loops and the underlying web of fused fibers. In these examples the upper extent of the web, from which the loops extend, is generally discernable. As illustrated by the photographs, the product provides an extensive field of hook-engageable loop fibers 56 supported on anon-woven web 75 that is very thin in comparison to the loft of the loops. As is particularly discernable in FIG. 2, the outer web (fastening) surface from which the loop fibers extend features a multitude of visually discrete fibers entangled to form the web. Thus, the loop product's fastening surface provides a cloth-like appearance desired in many applications involving wearable garments. As will be discussed further below, the loops themselves extend from entanglements in the web, and in many cases several loops extend from a common entanglement.

A particularly high proportion of the mass of fibers 12 lies above the web in the form of engageable loops 56, and in a portion of the volume occupied by loops above the web that is generally open and accessible to conventional male fastener elements, such as J-hooks, palm-tree hooks, or mushrooms. There is a sufficient proportion of fiber (and/or other materials) in web 75 to give the web dimensional stability within its plane and to provide sufficient tensile strength for processing and adequate resistance to loop pullout for many fastening applications.

Figure 3:
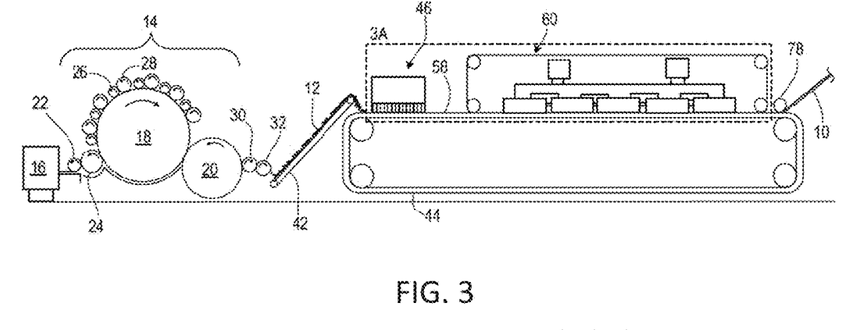
FIG. 3 is a diagrammatic plan view of a process for forming loop product.

FIG. 3 illustrates a machine and process for producing loop material 10. Beginning at the upper left end of FIG. 3, a carded web of fibers 12 is created by an initial carding stage. As shown, weighed portions of staple fibers are fed to a carding station 14 by a card feeder 16. In this example, carding station 14 includes a 50-inch main cylinder 18 and a 27-inch doffer 20. The card feedroll drive includes a 2.25-inch feed roll 22 and a 9-inch lickerin roll 26 that transfers the fibers to main cylinder 18. An alternating pattern of 3-inch stripper rolls 26 and 6-inch worker rolls 28 is distributed along the peripheral surface of main cylinder 18. In this example, carding station 14 includes six worker-stripper pairs, with the stripper rolls driven at a surface speed two to three times faster than the worker rolls. Doffer 20 transfers carded web 12 to a 6-inch condenser roll 30, and a take-off roll 32 deposits the carded web on a conveyor 42.

While the configuration shown and described herein is illustrative of an example carding station for providing lengthwise-incoherent fibers suitable for use in conjunction with various techniques presently disclosed, it should be understood that other methods of providing such lengthwise-incoherent fibers are also contemplated (e.g., alternative carding and air lay configurations).

During carding, the fibers are separated and combed into a cloth-like continuous layer consisting primarily of parallel fibers oriented to extend primarily along a length of the layer (carded web 12). The mat has virtually no strength when pulled in any direction because the fibers have been disentangled and are otherwise untethered. Thus, carded web 12 emerges from the carding station 14 as a "lengthwise-incoherent" layer of staple fibers, having little to no dimensional stability in the lengthwise direction, and will pull apart if attempted to be lifted from the conveyor.

In some embodiments, suitable fibers for forming the loop product 10 are drawn and crimped fibers, 1.5 to 6 denier, of about 1-inch (about 2.5 centimeters) to 4-inch (about 10 centimeters) staple length. Various synthetic or natural fibers may be employed. For example, in some applications, combinations of natural fibers, such as wool and cotton, and synthetic, thermally fusible fibers, may provide sufficient loop strength. Presently, however, thermoplastic staple fibers which have substantial tenacity are preferred for making thin, low-cost loop product that has good closure performance when paired with very small molded hooks. Suitable thermoplastic materials may include polymers, such as polyesters, polyamides, polyolefins (e.g., polypropylene and polyethylene), acrylics, and rayon, as well as blends and copolymers of such polymers. In some embodiments, the carded web includes one or more multicomponent fibers. Some multicomponent fibers are bicomponent fibers feature an outer sheath and an inner core. Suitable bicomponent fibers may include bicomponent polyester fibers and bicomponent polyethylene/polyester fibers. In some implementations, it may be particularly advantageous to employ bicomponent fibers having a broad bonding window, where the inner core material has a much higher melting point than the outer sheath material. In some embodiments, a blend of different types of fibers may be used. For example, a suitable fiber blend may include at least one "binder fiber" (i.e., a fiber having a particularly low melt temperature) and one or more "loop fibers" having relatively higher melt temperature and tenacity suitable for engagement with male fastener elements. For example, the polyethylene sheath of a suitable bicomponent fiber may have a melting temperature of about 266° F. (about 130° C.) and the polyester core may have a melting temperature of about 485° F. (about 252° C.). For a product having some electrical conductivity, a small percentage of metal fibers may be added. For instance, loop products of up to about 5 to 10 percent fine metal fiber, for example, may be advantageously employed for grounding or other electrical applications. In some embodiments, the composition of a fiber blend may include at least 50 percent binder fiber.

Loop fibers with tenacity values of at least 1.1 grams per denier have been found to provide good closure performance, and fibers with a tenacity of at least 5 or more grams per denier (preferably even 8 or more grams per denier) are even more preferred in many instances. In general terms for a loop-limited closure, the higher the loop tenacity, the stronger the closure. For many applications, particularly products where the hook-and-loop components will be engaged and disengaged more than once ("cycled"), it is desirable that the loops have relatively high strength so that they do not break or tear when the fastener product is disengaged. Loop breakage causes the loop material to have a "fuzzy," damaged appearance, and widespread breakage can deleteriously effect re-engagement of the fastener. Loop strength impacts closure performance and is proportional to fiber tenacity and denier. Fibers having a fiber titer of at least 1.5 to 6 denier and a tenacity of at least 1 to 7 grams/denier, provide sufficient loop strength for many applications. Where higher loop strength is required, fiber denier, tenacity, or both, may be increased. The loop fiber denier should be chosen with the hook size in mind, with lower denier fibers typically selected for use with smaller hooks. In applications for use with larger hooks, larger fiber titer and/or higher tenacity may be employed.

Referring again to FIG. 3, carded web 12, in its lengthwise-incoherent state, is carried up conveyor 42 and deposited on a brush apron 44. In some embodiments, brush apron 44 is provided in the form of a continuous belt supporting a dense bed of upstanding flexible bristles. As shown, brush apron 44 is maintained to travel at a constant line speed along a linear path while carrying carded web 12 through various stations of the manufacturing process. In this example, brush apron 44 initially carries the dispensed carded web 12 to a needling station 46, where the carded web is repeatedly needle-punched. The needles may be guided through a stripper plate above the fibers, and draw small pouches of fibers through the carded web to form loops on the opposite side. During needling, carded web 12 is supported directly on the bristles of brush apron 44 (as shown in FIGS. 4A-4D), which moves with the carded web through needling station 46. In some embodiments, needling station 46 needles carded web 12 with an overall penetration density of about 40 to 160 punches per square centimeter.

In some embodiments, needling station 46 may be provided in the form of a "structuring loom" configured to subject the fibers of carded web 12 to a random velour process. Thus, the needles penetrate a moving bed of bristles arranged in an array (brush apron 44). In some implementations, the needling station may feature a double-beam, random-velour needle loom. In a particular implementation, needle beams are fitted with needle boards having a density of 7500 needles/meter. In this implementation, the needle loom was fitted with 40 gauge, 2.5 inch needles cycled at a stroke amplitude of 40 millimeters and a stroke frequency of 2100 strokes per minute. In some implementations, the needling station may feature two consecutive double-beam looms.

In some embodiments, brush apron 44 may have a nominal bristle density of about 2500 bristles per square inch (about 380 bristles per square centimeter). The bristles are each about 0.008 inch (0.2 millimeter) in diameter and about 20-25 millimeters long, and are preferably straight with rounded tips. In some embodiments, brush apron 44 includes a plurality of discrete brush segments 45 (see FIG. 3A) secured to aluminum slats driven by a continuous belt over a supporting steel deck. Alternatively, in some alternative embodiments, the bristles of brush apron 44 are directly attached to the continuous belt. The bristles may be formed of any suitable material, for example 6/12 nylon. Suitable brushes may be purchased commercially and retrofitted onto suitable looms. Generally, the brush apron moves at the desired line speed.

Figure 4A:
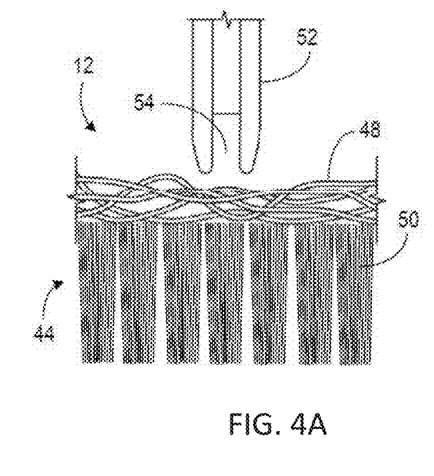
FIGS. 4A-4D are progressive diagrammatic side views detailing a needling stage of the process of FIG. 3.
Figure 4B:
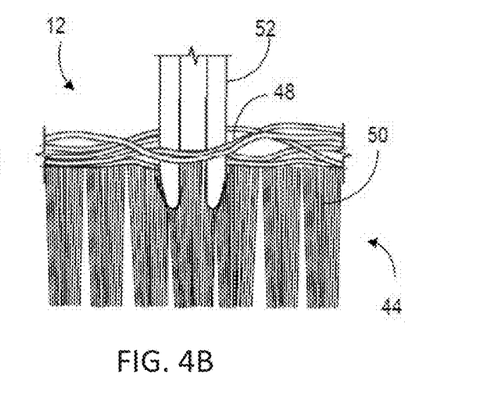
Figure 4C:
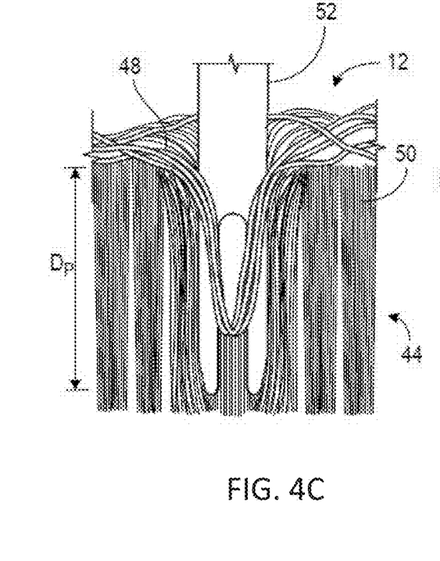
Figure 4D:
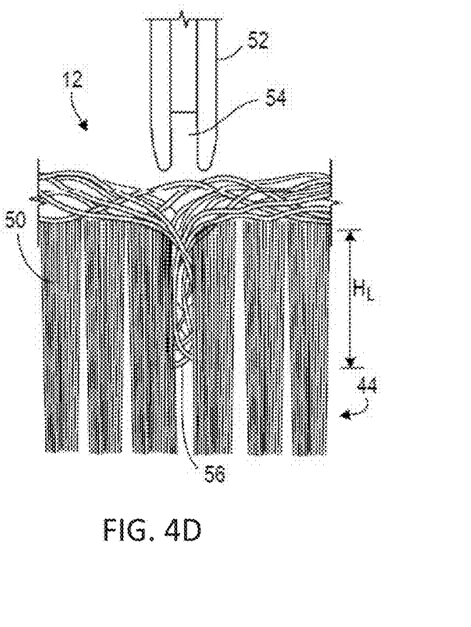

FIGS. 4A through 4D sequentially illustrate the formation of a loop structure by a suitable needling process, such as may be performed at needling station 46. Initially, carded web 12 is conveyed to the needling station by brush apron 44, with the individual fibers 48 of the carded web carried directly on a bed of brush bristles 50 (FIG. 4A). As a fork needle 52 enters carded web 12 (FIG. 4B), some individual fibers 48 will be captured in the cavity 54 between the leading prongs of the forked end of the needle. As needle 52 "punches" through the carded web, these captured fibers 48 are drawn down with the needle into the bed of brush bristles 50. As shown, carded web 12 remains generally supported on brush apron 44 through this process. Thus, the penetrating needle 52 laterally displaces local brush bristles 50 as it intrudes upon brush apron 44. As needle 52 continues to penetrate (FIG. 4C) through brush bristles 50, tension is applied to the captured fibers 48, drawing them tightly around the penetration point. In this example, a total penetration depth "$D_p$" of up to about 10 millimeters, as measured from the top surface of brush apron 44, was found to provide a well-formed loop structure without overly stretching fibers in the remaining web. Excessive penetration depth can draw loop-forming fibers from earlier-formed tufts, resulting in a less robust loop field. Penetration depths of 2 to 10 millimeters may also be implemented in this example, with 2 millimeters to 4 millimeters penetration being presently preferred. When needle 52 is retracted from the bristle bed (FIG. 4D), the portions of the captured fibers 48 carried through brush bristles 50 remain in place having the form of a plurality of individual loops 56 effectively clamped between previously displaced—now recovered— bristles. With a punch depth of 2.5 mm, the resulting loop formation has an overall height "$H_L$" of about 0.040 to 0.060 inch (1 to 1.5 millimeters), measured optically prior to compression or spooling and while the loop product is free of any load, for engagement with the size of male fastener elements commonly employed on disposable garments and such. It should be understood that additional needle types may be used; for example, felting needles or crown needles.

Advance of the carded web per needle stroke is limited due to a number of constraints, including needle deflection and potential needle breakage. Thus, it may be difficult to accommodate increases in line speed and obtain an economical throughput by adjusting the advance per stroke. As a result, the alignment of the unbonded fibers may be disturbed due to the travel of the web on the brush apron during penetration of the needle. For applications in which this effect is undesirable, an elliptical needling technique (such as described in U.S. Pat. No. 7,465,366 the entirety of which is incorporated herein by reference), or similar, can be used to reduce or eliminate relative movement between the web and the penetrating needles. Using elliptical needling, it may be possible to obtain line speeds of 60 mpm (meters/minute) or greater, e.g., 120 mpm. Such speeds may be obtained with minimal disturbance of the unbonded fibers.

For needling longitudinally discontinuous regions of the material, such as to create discrete loop regions, the needle boards can be populated with needles only in discrete regions, and the needling action paused while the material is indexed through the loom between adjacent loop regions. Effective pausing of the needling action can be accomplished by altering the penetration depth of the needles during needling, including to needling depths at which the needles do not penetrate the carded web. Such needle looms are available from Autefa Solutions in Austria, for example. Alternatively, means can be implemented to selectively activate smaller banks of needles within the loom according to a control sequence that causes the banks to be activated only when and where loop structures are desired. Lanes of loops can be formed by a needle loom with lanes of needles separated by wide, needle-free lanes.

Figure 3A:
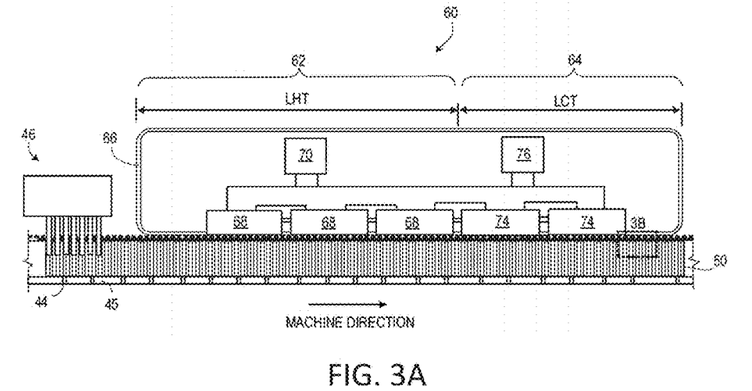
FIG. 3A is diagrammatic plan view of a portion of the process of FIG. 3 marked 3A.

Referring back to FIG. 3, the needled product 58 leaves needling station 46 in an unbonded state, and proceeds to a bonding station 60 while the loops 56 of fibers remain engaged within the bristle bed of brush apron 44. At bonding station 60, portions of fibers exposed on the surface of the bristle bed, opposite the loops held by the bristles of brush apron 44, are at least partially fused to create a dimensionally stable base layer of the product. As illustrated in FIG. 3A, bonding station 60 includes a heating section 62 and a cooling section 64 integrated by a single, continuous conveyor belt 66, for example a Teflon® belt or a belt with similar heat-transfer and release properties. Heating section 62 includes a bank of heating modules 68 operated by a controller 70. Similarly, cooling section 64 includes a bank of cooling modules 74 operated by a controller 76. Conveyor belt 66 rides against the respective heating and cooling modules 68, 74 while simultaneously contacting needled product 58 to facilitate a bonding process with appropriate heating/cooling under pressure. During the bonding process the surfaces in contact with each side of the product (e.g., conveyor belt 66 and brush apron 44) move at the same longitudinal speed, avoiding relative motion at the fibers. Thus, conveyor belt 66 is operated to match the line speed of brush apron 44 to avoid disturbing the needled fibers with relative motion.

Figure 3B:
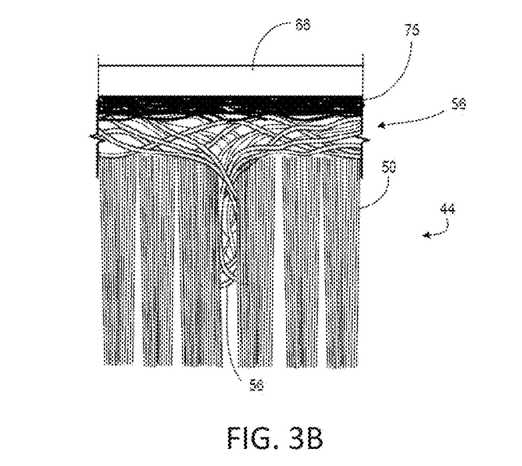
FIG. 3B is a diagrammatic side view of a bonding stage of the process of FIG. 3A marked 3B.

FIG. 3B provides an example illustration of needled product 58 sandwiched between conveyor belt 66 and the bristles 50 of brush apron 44. As shown, heat applied to the exposed fibers outside the brush apron 44 creates a partially melted and fused fibrous web 75, while the loops 56 of fibers secured between the bristles remain substantially unbonded. In some implementations, there may be a transition zone between the denser, fused layer on the backside of the needled product 58 and the unfused layer on the front resting against the brush apron 44 where there is gradually less melting and fusing of the staple fibers. The characteristics of this transition zone (e.g., degree of melting and fusing, thickness, etc.) may vary with different process parameters. In some implementations, when bicomponent fibers are used, the bonding parameters may be selected so that only the outer sheaths of the bicomponent fibers are melted. Thus, the sheaths of the bicomponent fibers act as an adhesive agent to bond the fibers together, while the cores of the fibers remain substantially intact, maintaining their integrity. Further, in some examples, the melting and reforming of the outer sheaths at or near the base of the loops tends to support the cores of the fibers in an upright position when the loop structures are pulled from the brush apron.

Returning to FIG. 3A, in some embodiments, the heating and cooling modules 68, 74 may be operated by the respective controllers 70, 76 individually or in subgroups of staged heating/cooling zones along the length and/or width of the heating and cooling conveyor belts 66, 72. In some embodiments, heating modules 68 are operated such that the heating zones provide a steadily increasing temperature profile in the "machine direction" (i.e. the direction of travel of the needled product as it is carried through the heating section on the brush apron 44). The progressive temperature profile may create the effect of a gradual "heat soak" that steadily heats the exposed fibers (at least) up to an "activation temperature" (e.g., a melting or softening temperature of the outer sheath of a bicomponent fiber) at which the fibers begin to fuse together under relatively light pressure applied by the heating conveyor belt. As one example, to achieve fusing at an activation temperature of 300° F., the following heat profile provided in Table 1 may be used:

TABLE 1

| Heating Zone | Temperature |
| --- | --- |
| Heating Zone 1 | 125° F. (about 52° C.) |
| Heating Zone 2 | 200° F. (about 93° C.) |
| Heating Zone 3 | 250° F. (about 121° C.) |
| Heating Zone 4 | 300° F. (about 149° C.) |
| Heating Zone 5 | 300° F. (about 149° C.) |
| Heating Zone 6 | 300° F. (about 149° C.) |
| Heating Zone 7 | 200° F. (about 93° C.) |

In the illustrated configuration, the bonding pressure exerted by the conveyor belt may be restricted to a relatively low level in order to avoid damage to the delicate needled product and the supporting bristles of the brush apron. The progressive heat soak achieved by light pressure contact with the conveyor belt over a relatively long dwell time (which may be achieved by providing a relatively lengthy heating section and/or a slower line speed) may provide consistent melting and amalgamation of the exposed fibers, which, after cooling, produces a cohesive and relatively flat fused web 75 (see FIG. 3B). This process configuration may also yield mitigating effects on curl and/or shrinkage in the cross-machine direction (widthwise) of the product.

In a particular example, the heating section may be configured having a heating tunnel length ($L_{HT}$) of about 3.5 meters, with 2.0 heating modules operated to create 5 staged temperature zones along the length of the conveyor belt and three staged temperature zones along the 1.6 meter width of the conveyor belt. The heating modules may be operated to create temperature zones ranging from about 70° F. to about 400° F. The line speed of the brush apron may be about 20 meters/minute to provide a dwell time in the heating section of about 11 seconds. Further, in this example, the cooling section was configured having a cooling tunnel length ($L_{CT}$) of about 1.5 meters, with 10 cooling modules. The cooling modules may be operated to create temperature zones of about 35° F. to about 70° F.

Referring back to FIG. 3, the loop product 10 leaves the bonding station 60 as a lengthwise-coherent sheet-form article having sufficient dimensional stability to be removed from brush apron 44 via tension applied by a stripper roll 78, which pulls the loops 56 of fibers from the bed brush bristles. Removed from brush apron 44, loop product 10 features a fastening layer having a plurality of exposed fastening loops extending from an underlying fused web.

Figure 9:
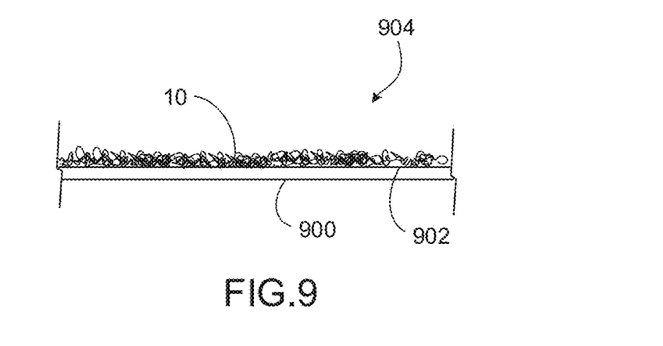
FIG. 9 is a side view of a touch fastener formed as a laminate of the loop product and a backing Like reference symbols in the various drawings indicate like elements.

Loop material 10 is suitable for spooling and transport to a facility where it can be unrolled and laminated directly to a product surface, such as a non-woven diaper chassis. In some cases, prior to spooling a thin, non-porous backing film is laminated to the fused (back) side of the web to form a substantially impermeable product that can be subsequently processed using vacuum transport. In another example, a film, such as a polyolefin film of about 0.001 inch (0.025 mm) in thickness, and with a basis weight of 0.369 osy (12.5 gsm), is laid over the needled web before it enters the bonding station, and is fused in situ to the fibers to become part of the fused web. Other materials can be bonded to the web, either as the fibers are fused or in a subsequent lamination process. Examples of such materials include other films, such as elastomeric or stretchable films, other non-woven materials, and paper. For example, FIG. 9 shows the loop material adhesively laminated to an air-impermeable backing 900 by a separate adhesive 902, to form a touch fastener 904.

Other details of the above process can be found in pending U.S. patent application Ser. No. 14/610,625 "Needling Fibrous Webs," filed Jan. 30, 2015, the entire contents of which are incorporated herein by reference.

Figure 5:
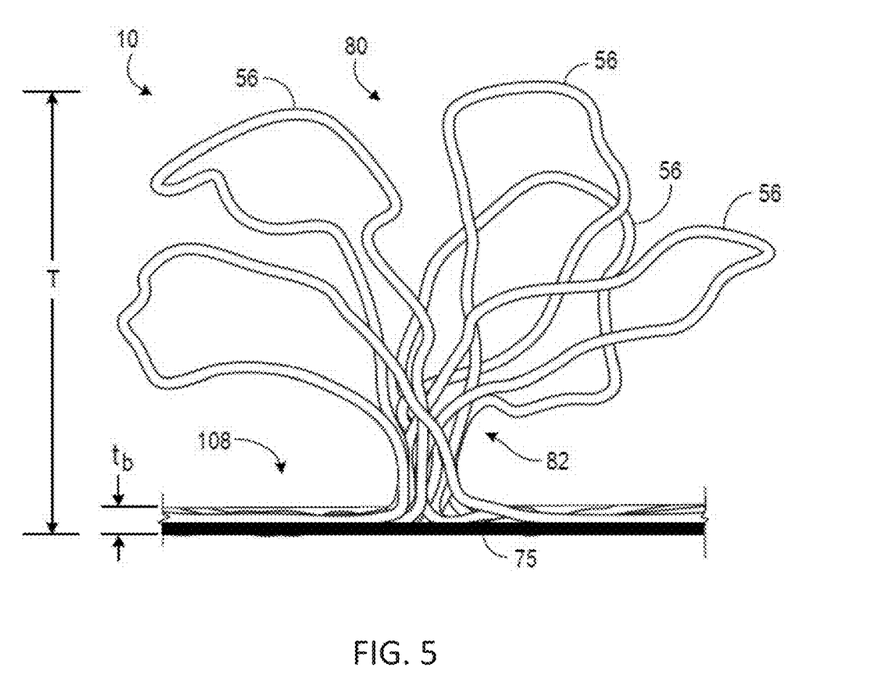
FIG. 5 is a highly enlarged diagrammatic side view of loop structure formed by process of FIG. 3.

FIG. 5 is an enlarged schematic view of a loop structure 80 containing multiple loops 56 of individual fibers extending from a common trunk 82 extending from the upper surface 108 of a web 75 of fused fibers, as formed by the above-described process. This view is intended to illustrate a general type of structure that can result from needling, and is not meant to imply that all, or even a majority of the loops in the resulting loop field will be discernibly part of such a structure. In many cases, availability of loops 56 for engagement with a mating hook product is believed to be enhanced by vertical stiffness of trunk 82 of the formation, which is augmented by the anchoring of the fibers at the web. Preferably, the web is fused such that each loop fiber is bonded at multiple points to other fibers within the web, to provide sufficient resistance to loop pull-out during fastening uses, and to provide sufficient peel strength and shear strength. Further, as noted above, the needling process tends to draw the fibers taught around the point of penetration, which creates the stiffness in the trunk when the opposing ends of the loop fibers are fused within the web. This vertical stiffness acts to resist permanent crushing or flattening of the loop structures, which can occur when the loop material is spooled or when the finished product to which the loop material is later joined is compressed for packaging. Resiliency of the trunk 82, especially at its juncture with web 75, enables structures 80 that have been "toppled" by heavy crush loads to right themselves when the load is removed. The various loops 56 of structure 80 extend to different heights from web 75, which is also believed to promote fastener performance. As each structure 80 is formed at a penetration site during needling, the density and location of the individual structures are very controllable. Preferably, there is sufficient distance between adjacent structures so as to enable good penetration of the field of formations by a field of mating male fastener elements (not shown). Each of the loops 56 is of a staple fiber whose ends are fused to surrounding fibers of web 75, such that the loops are each structurally capable of hook engagement.

In part because the entire loop product 10 is manufactured solely from staple fibers, it can be manufactured having high air permeability, low thickness and low weight with good closure performance characteristics. In some embodiments, web 75 can have a thickness "$t_b$" (see FIG. 5) of only about 0.015 inch (0.381 millimeter) or less, preferably less than about 0.005 inch (0.127 millimeter), and even as low as about 0.001 inch (0.025 millimeter) or slightly greater than the diameter of the fiber in some cases. The finished loop product 10 may have an overall thickness "T" of less than about 0.4 inch (10 millimeters), preferably less than about 0.16 inch (4 millimeters). The overall width of loop product 10 may be approximately the same overall width as the layer of staple fibers provided on the brush (i.e., not exhibiting significant signs of shrinkage). The overall weight of loop product 10, may be as low as 0.5 ounces per square yard (17 grams per square meter). In some embodiments, loop product 10 has a Frazier air permeability of at least 500 feet$^3$/feet$^2$/sec (150 m$^3$/m$^2$/sec). Preferably, loop product 10 has a peel strength of at least 500 grams force per inch width (in some cases, 650 grams force per inch width), and a shear strength of at least about 8,000 grams force per square inch, when tested with HTH725 hook available from Velcro USA Inc. in accordance with test methods under ASTM D5170-98 and ASTM D5169-98.

In addition to loop tenacity and loop strength (discussed above) that are determined by fiber selection, closure performance is dependent on the density and uniformity of the loop structures over the surface area of the loop product. The techniques described above may be particularly advantageous in this regard compared to other known processes where a carded web of staple fibers is supported on a carrier sheet during needling. As a result, we have found that the presently described techniques yield a superior conversion rate of needle penetrations to "functional loops" (e.g., loop structures 80 that are suitable for engagement with male fastener elements) per unit area of the needle-punched loop product, which corresponds to increased density and uniformity. Thus, in some implementations, the loop product resulting from the above-described techniques can offer comparable or superior closure performance with lower tenacity and/or lower denier staple fibers. Therefore, loop product 10 can provide a good balance of low cost, light weight and good closure performance.

In a particular implementation, a loop product manufactured from fiber ETC233 available from ES FiberVisions, Inc. of Athens, Ga. ETC233 is a 3.3 decitex, bicomponent fiber (55% polyester core, 45% polyethylene sheath) featuring 15 crimps per inch, a nominal fiber length of 51 mm, and tenacity of 2.7 cN/decitex. The fiber was processed in accordance with the above-described techniques, including needling to a needling density of 80 penetrations per square cm with 40 gauge, forked needles cycled to a penetration depth of 6 mm, was measured to have an overall thickness of approximately 0.055 inch and a basis weight of about 32 grams per square meter (about 0.94 ounces per square yard). This loop product exhibited the following characteristics summarized in Table 2:

TABLE 2

| | |
|---|---|
| Peel Strength (Tested with HTH725 under ASTM D5170-98) | 700 gram-force/inch (about 275 gram-force/centimeter) |
| Shear Strength (Tested with HTH725 under ASTM D5169-98) | 8,686 gram-force/inch$^2$ (about 1,346 gram-force/centimeter$^2$) |
| Air Permeability | 784 feet$^3$/feet$^2$/sec (239 m$^3$/m$^2$/sec) |
| Break Strength - Machine Direction | 5.8 pounds-force (about 25.8 Newtons) |
| Percent Elongation - Machine Direction | 51% |

TABLE 2-continued

| | |
|---|---|
| Break Strength - Cross Machine Direction | 1.1 pounds-force (about 4.9 Newtons) |
| Percent Elongation - Cross Machine Direction | 60% |
| Critical Fiber Volume Percentage (CFVP) | 34% |
| Maximum Fiber Volumetric Ratio (MFVR) | 12.9% |

Determining Maximum Fiber Volumetric Ratio (MFVR)

The following is a protocol by which MFVR is determined for a given loop material, the loop material from which specimens are prepared is provided on a roll, the outer lap of the roll should be removed and discarded. If the loop material is provided adhered to a surface of a product, such as a surface of a diaper, the loop material should be removed from the surface prior to testing. For example, a loop material adhered to a diaper chassis can often be removed without damage to the loop material by spraying the loop material with chilled carbon dioxide spray to deaden and release the adhesive. To remove a loop material from a diaper chassis, first open the diaper and place it on a flat surface, such as a table, such that the entire loop patch is exposed. Spray the face of the loop patch for two seconds with an aerosol coolant spray, such as CRC Freeze Spray, available from CRC industries in Warminster, Pa. The loop patch should then peel off easily by gripping a small portion on one end of the loop patch and peeling it from the chassis.

Whether cut from a roll or removed as a small patch from another material, the specimen should be conditioned in an atmosphere for testing of 23±2° C. (73.4° F.±3.6° F.) and 50±5% relative humidity as described in ASTM Practice D 618 for a period of 24 hours or until the specimen reaches moisture equilibrium. Lay specimens out with the functional loop side up so that the conditioning atmosphere has free access to the loop fibers.

Prior to mounting the specimen for CT analysis, the specimen should be further prepared by the following fiber-lifting procedure. First, the specimen is secured over a flat surface using tape at one end. A flat scraping edge, in the form of a steel block having an overall mass of 0.23 kg and a rectangular contact surface of dimensions 32 mm by 0.5 mm and a leading edge radius of about 0.1 mm is placed on the loop material adjacent the taped end. The contact surface should be in full contact with the loop material and should be oriented such that in the subsequent dragging process the block is dragged in the direction of its short dimension across the loop material. The fiber-lifting procedure is completed by dragging the block along the length of the specimen, under only its own weight, at a rate of about 30 cm/sec, twice in the same direction. Between passes the block is lifted from the specimen, such that the specimen is only subjected to the scraping process in one direction.

Figure 6:
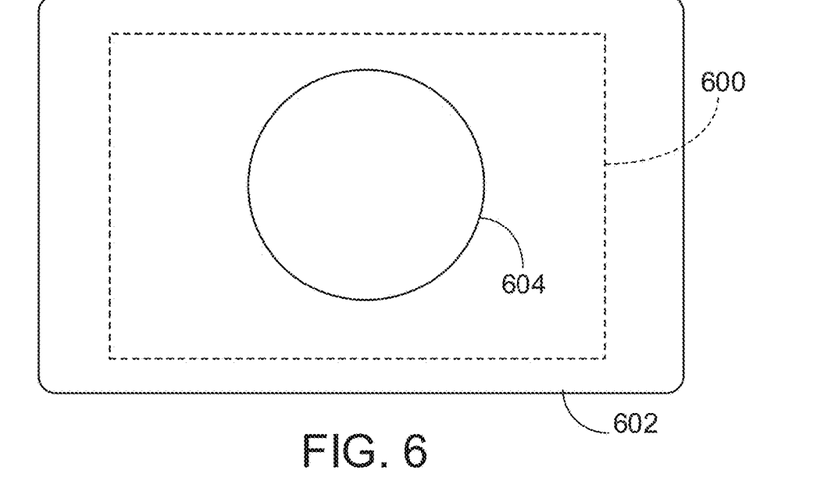
FIG. 6 is a top view of a specimen of loop material mounted to a support card.
Figure 7:
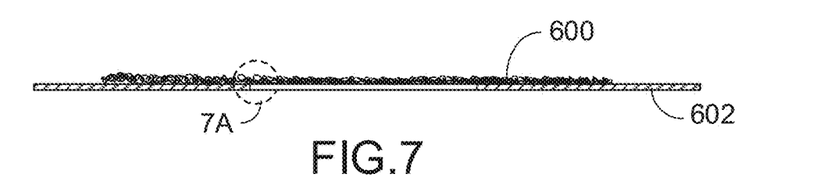
FIG. 7 is a side view of the mounted loop specimen.
Figure 7A:
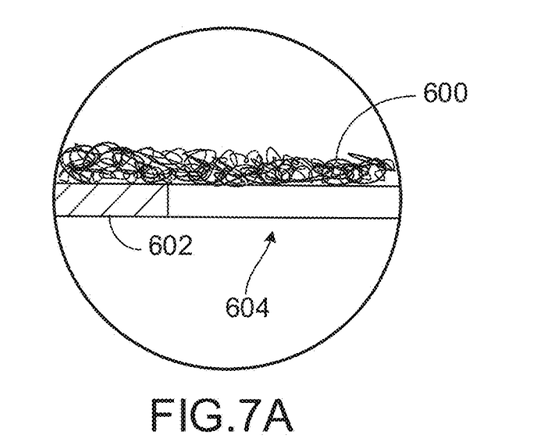
FIG. 7A is an enlarged view of area 7A of FIG. 7.

Referring to FIGS. 6-7A, mount each specimen 600 to a separate 1/16 inch (1.5 mm) thick flat carbon fiber support 602 defining a 0.75 inch (19 mm) hole 604 over which the loop specimen 600 is centered. The specimen may be bonded with any adhesive that does not migrate into the loop material directly over the hole 604 but that keeps the loop material secured to the support 602 during measurement. The loop material should be mounted with no visible wrinkling or puckering, in a generally planar state, and with the fastening (functional) surface facing away from the support. (If the specimen has two hook-engageable loop surfaces, the one with greater loft should face away from the support.) Allow the adhesive to set, as needed. During the mounting process and throughout the following scanning, the portion of the loop material specimen over the hole should not be touched or compressed.

By X-ray Computed Tomography (CT) methods, tomographic images (virtual 'slices') of a test area of the specimen 600 are generated. Equipment to be used for this purpose is a Nikon XTHST 225 CT machine fitted with a Perkin Elmer 1621EHS digital panel option, or functional equivalent. An initial scan is conducted over an area of 12 mm by 12 min. if an initial scan determines that the sample backing is not flat then alignment should be corrected physically prior to proceeding further with the test. Once satisfied that the sample is flat a final scan is conducted over the 12×12 mm area. The backing of this scan area is then further analyzed to identify what visually appears to be the flattest portion of the sample, this comprises the Test Area. A representative Test Area may be 4×3 min, or 11×5 mm, or for example if only a small portion is flat the size may be 1.5×1.5 mm. Although the sample must be flat it does not need to be parallel to the plane of the support or the plane of scanning as this may be corrected electronically after the scan. This angle is corrected by identifying 20 points that comprise the bottom of the base of the sample. The plane that best fits to these 20 points is generated and this serves as the zero position for all orthogonal scans.

The Test Area over which the following measurement is to be made is a reasonably planar portion of the specimen within the area of the support hole, encompassing any repeating pattern in the material, and representing the overall material. For example, if the overall material has bond areas encompassing 30% of its overall area, the Test Area should be selected to have a similar 30% bond area coverage. For materials having large repeating patterns, multiple measurements may be taken over adjacent areas and averaged to cover a full repeat of the pattern. Planar X-ray CT images are generated at six-micron increments, parallel to the surface of the support. The lowermost image is taken below the lowermost extent of the sample material, and the uppermost image is at an elevation above the highest loop. (Note, it will be generally found that the highest images are not necessary for determining MFVR.) Each Slice Fiber Volume is calculated as the area occupied by material at the plane of the slice, projected over a six-micron elevation. The Slice Fiber Volume of each image is tabulated with a corresponding Slice Reference Position (the elevation of the lower side of the slice). For example, a Slice Reference Position of zero corresponds to a Slice Fiber Volume finning from a lowermost elevation of sample fiber up six microns into the base. At each Slice Reference Position, the Fiber Volumetric Ratio is calculated as the Slice Fiber Volume divided by the total volume of the slice (i.e., the product of the test area and the thickness of the slice, in this case six microns). From the tabulated Fiber Volumetric Ratios, the Slice Reference Position (and thus, the elevation) of the Maximum Fiber Volumetric Ratio (MFVR) is determined.

Figure 8:
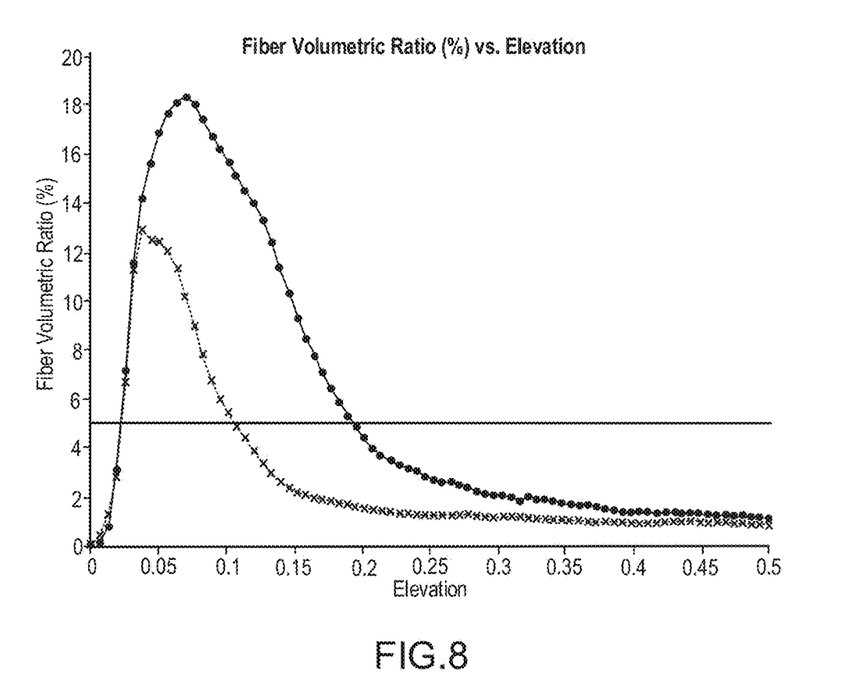
FIG. 8 is a graph of Fiber Volumetric Ratio for two sample loop products.

For example, here is a table of measurements of two sample loop materials. The MFVR of 12.9% (Sample A) and 18.3% (Sample B) are highlighted in bold, and occur at elevations of 0.038 mm and 0.069 min, respectively. Fiber Volumetric Ratio fur each of the samples is plotted as a function of elevation in FIG. 8.

|  | Sample A | | Sample B | |
| --- | --- | --- | --- | --- |
| Slice Reference Position (mm) | Slice Fiber Volume | Fiber Volumetric Ratio | Slice Fiber Volume | Fiber Volumetric Ratio |
| 0.00000000 | 0.00018 | 0.0% | 0.00010 | 0.0% |
| 0.00631849 | 0.00202 | 0.4% | 0.00082 | 0.2% |
| 0.01263698 | 0.00733 | 1.3% | 0.00398 | 0.7% |
| 0.01895547 | 0.01614 | 2.9% | 0.01656 | 3.1% |
| 0.02527396 | 0.03714 | 6.7% | 0.03831 | 7.2% |
| 0.03159245 | 0.06320 | 11.4% | 0.06190 | 11.6% |
| 0.03791094 | 0.07181 | 12.9% | 0.07575 | 14.1% |
| 0.04422943 | 0.06944 | 12.5% | 0.08360 | 15.6% |
| 0.05054792 | 0.06916 | 12.5% | 0.09026 | 16.9% |
| 0.05686641 | 0.06684 | 12.0% | 0.09447 | 17.6% |
| 0.06318490 | 0.06289 | 11.3% | 0.09666 | 18.0% |
| 0.06950339 | 0.05657 | 10.2% | 0.09795 | 18.3% |
| 0.07582188 | 0.04985 | 9.0% | 0.09683 | 18.1% |
| 0.08214037 | 0.04357 | 7.8% | 0.09362 | 17.5% |
| 0.08845886 | 0.03779 | 6.8% | 0.08979 | 16.8% |
| 0.09477735 | 0.03341 | 6.0% | 0.08704 | 16.3% |
| 0.10109584 | 0.03020 | 5.4% | 0.08406 | 15.7% |
| 0.10741433 | 0.02740 | 4.9% | 0.08100 | 15.1% |
| 0.11373282 | 0.02452 | 4.4% | 0.07781 | 14.5% |
| 0.12005131 | 0.02161 | 3.9% | 0.07502 | 14.0% |
| 0.12636980 | 0.01897 | 3.4% | 0.0714 | 13.3% |
| 0.13268829 | 0.01660 | 3.0% | 0.06661 | 12.4% |
| 0.13900678 | 0.01466 | 2.6% | 0.06101 | 11.4% |
| 0.14532527 | 0.01327 | 2.4% | 0.05550 | 10.4% |
| 0.15164376 | 0.01222 | 2.2% | 0.04989 | 9.3% |
| 0.15796225 | 0.01162 | 2.1% | 0.04546 | 8.5% |
| 0.16428074 | | | 0.04156 | 7.8% |
| 0.17059923 | | | 0.03785 | 7.1% |
| 0.17691772 | | | 0.03456 | 6.5% |
| 0.18323621 | | | 0.03137 | 5.9% |
| 0.18955470 | | | 0.02842 | 5.3% |
| 0.19587319 | | | 0.02612 | 4.9% |
| 0.20219168 | | | 0.0233 | 4.4% |
| 0.20851017 | | | 0.02107 | 3.9% |
| 0.21482866 | | | 0.01952 | 3.6% |
| 0.22114715 | | | 0.01848 | 3.5% |
| 0.16428074 | | | 0.00010 | 0.0% |
| 0.17059923 | | | 0.00082 | 0.2% |
| 0.17691772 | | | 0.00398 | 0.7% |
| 0.18323621 | | | 0.01656 | 3.1% |
| 0.18955470 | | | 0.03831 | 7.2% |

Determining Rising and Falling 5% Ratio Elevations

The elevations where the Fiber Volumetric Ratio first rises above 5%, and then falls back below 5% are the Rising 5% Ratio Elevation and the Falling 5% Ratio Elevation, respectively. From the table above, Sample A has a Rising 5% Ratio Elevation of 0.025 mm and a Falling 5% Ratio Elevation of 0.107 mm, while Sample B has a Rising 5% Ratio Elevation of 0.025 mm and a Falling 5% Ratio Elevation of 0.196 mm. In each sample, the maximum Fiber Volumetric Ratio occurs closer to the Rising 5% Ratio Elevation than to the Falling 5% Ratio Elevation.

The difference between these two values for a given sample represents the normal elevation span over which the Fiber Volumetric Ratio remains above a critical threshold of five percent. For Sample A, this span is 0.107-0.025 or 0.082 mm, and for sample B this span is 0.196-0.025 or 0.171 mm. Preferably, the MFVR occurs within a lower 30 percent of this elevation span.

Determining Product Thickness

Test the thickness of each specimen according to ASTM D1777-96 (Reapproved 2011). This includes preconditioning the specimen by bringing it to approximate moisture equilibrium in standard atmosphere for preconditioning textiles, and then bringing the specimen to moisture equilibrium for testing in the standard atmosphere for testing textiles, both as specified in ASTM Practice D1776. Weigh each specimen to determine its weight (W) in grams. Following the procedure outlined in TM D1777-96 (Reapproved 2011), Option 5 (0.1 psi), determine the thickness of the specimen.

Determining Critical Fiber Volume Percentage (CFVP)

Using the same specimen preparation and X-Ray CT methods discussed above, the Test Volume is determined as the volume of the test area (within the plane of the specimen) projected over the orthogonal distance between the lowest and highest elevations of sample material within the test area. If an initial scan determines that the sample is generally aligned with a plane not parallel to the plane of the scanning, the alignment should be corrected, either physically or by electronic reorientation prior to the final data scan. Total Sample Volume (TSV) is the total volume of material within the Test Volume. By 'sample material' we mean the fibers entangled to form the loops and interconnecting web between the loops, and any other material within the web or otherwise not removable from the web without destruction of the web itself. Thus, in specimens in which the base web of the loop material contains binder embedded between sample fibers, the TSV will include the binder. Similarly, if the specimen includes other material (e.g., foam, ink) between the loops, the TSV will include the volume of those materials. If the specimen includes a backing that can be released by deactivation of adhesive, for example, such a backing should be removed before testing.

From the tabulated Fiber Slice Volumes as generated above with respect to the calculation of Maximum Fiber Volumetric Ratio, the maximum Slice Fiber Volume and an elevation corresponding to the maximum Slice Fiber Volume are determined. Each Slice Fiber Volume in the table is normalized to a percentage of the maximum Slice Fiber Volume.

Proceeding back to front with respect to the specimen, a running total of Slice Fiber Volumes is calculated and added to the table. The running total of Slice Fiber Volumes comprises the total volume of solid material at or below a given Slice Reference Position.

For each image, the Running Percentage (RP) is calculated by dividing the corresponding running total of Slice Fiber Volumes by the TSV and multiplying by 100, and added to the table.

The Critical Fiber Volume Percentage (CFVP) is identified as the Running Percentage (RP) corresponding to an elevation where, moving upward with respect to the specimen from an elevation corresponding to the maximum Slice Fiber Volume, the percentage of the maximum Slice Fiber Volume first drops to below 70%.

For example, here is a table of measurements of a specimen (Sample A of the above table) having a total sample volume of 1.70082 cubic millimeters. The maximum Slice Fiber Volume is highlighted in bold, as is the entry where the percentage of the maximum Slice Fiber Volume falls to below 70%, and the resulting Critical Fiber Volume Percentage (far right column). Based on this data, the CFVP of this material would be 33.7%.

| Slice Reference Position (inch) | Slice Fiber Volume | Percentage of TSV | Percent of maximum Slice Fiber Volume | Running total of Slice Fiber Volume | Running Percentage (RP) |
|---|---|---|---|---|---|
| 0.00000000 | 0.00018 | 0.01058313 | 0.25066147 | 0.00018 | 0.010583130 |
| 0.00631849 | 0.00202 | 0.11876624 | 2.81297869 | 0.00220 | 0.129349373 |
| 0.01263698 | 0.00733 | 0.43096859 | 10.2074920 | 0.00953 | 0.560317964 |
| 0.01895547 | 0.01614 | 0.94895403 | 22.4759783 | 0.02567 | 1.509271998 |
| 0.02527396 | 0.03714 | 2.18365259 | 51.7198162 | 0.06281 | 3.692924589 |
| 0.03159245 | 0.06320 | 3.71585471 | 88.0100265 | 0.12601 | 7.408779295 |
| 0.03791094 | 0.07181 | 4.22208111 | 100.000000 | 0.19782 | 11.63086041 |
| 0.04422943 | 0.06944 | 4.08273656 | 96.6996240 | 0.26726 | 15.71359697 |
| 0.05054792 | 0.06916 | 4.06627391 | 96.3097062 | 0.33642 | 19.77987089 |
| 0.05686641 | 0.06684 | 3.92986912 | 93.0789584 | 0.40326 | 23.70974001 |
| 0.06318490 | 0.06289 | 3.69762820 | 87.5783317 | 0.46615 | 27.40736821 |
| 0.06950339 | 0.05657 | 3.32604273 | 78.7773291 | 0.52272 | 30.73341094 |
| 0.07582188 | 0.04985 | 2.93093919 | 69.4193009 | 0.57257 | 33.66435014 |
| 0.08214037 | 0.04357 | 2.56170553 | 60.6740008 | 0.61614 | 36.22605567 |
| 0.08845886 | 0.03779 | 2.22186945 | 52.6249826 | 0.65393 | 38.44792512 |
| 0.09477735 | 0.03341 | 1.96434661 | 46.5255535 | 0.68734 | 40.41227173 |
| 0.10109584 | 0.03020 | 1.77561412 | 42.0554240 | 0.71754 | 42.18788584 |
| 0.10741433 | 0.02740 | 1.61098764 | 38.1562456 | 0.74494 | 43.79887348 |
| 0.11373282 | 0.02452 | 1.44165755 | 34.1456622 | 0.76946 | 45.24053104 |
| 0.12005131 | 0.02161 | 1.27056361 | 30.0933018 | 0.79107 | 46.51109465 |
| 0.12636980 | 0.01897 | 1.11534436 | 26.4169336 | 0.81004 | 47.62643901 |
| 0.13268829 | 0.01660 | 0.97599981 | 23.1165576 | 0.82664 | 48.60243882 |
| 0.13900678 | 0.01466 | 0.86193718 | 20.4149840 | 0.84130 | 49.46437601 |

While a number of examples have been described for illustration purposes, the foregoing description is not intended to limit the scope of the invention, which is defined by the scope of the appended claims. There are and will be other examples and modifications within the scope of the following claims.

What is claimed is:

1. A touch fastener loop material comprising a non-woven web of fibers forming both a dimensionally stable base and a field of hook-engageable loops of a tenacity of at least 1.1 grams per denier extending outward from one broad side of the base, wherein the fibers are distributed such that the field of loops has a Maximum Fiber Volumetric Ratio of between 5 and 25 percent, and wherein the Maximum Fiber Volumetric Ratio occurs closer to the Rising 5% Ratio Elevation than to the Falling 5% Ratio Elevation.

2. The touch fastener loop material of claim 1, having a Critical Fiber Volume Percentage of between 20 and 60 percent.

3. The touch fastener loop material of claim 1, wherein the Maximum Fiber Volumetric Ratio is between 8 and 20 percent.

4. The touch fastener loop material of claim 3, wherein the Maximum Fiber Volumetric Ratio is between 10 and 15 percent.

5. The touch fastener loop material of claim 1, wherein the tenacity is at least 5 grams per denier.

6. The touch fastener loop material of claim 5, wherein the tenacity is at least 8 grams per denier.

7. The touch fastener loop material of claim 1, having a Peel Strength of at least 500 grams force per inch width when mated with an HTH725 hook and tested according to ASTM D5170-98.

8. The touch fastener loop material of claim 1, having a Shear Strength of at least 8,000 grams force per square inch when mated with an HTH725 hook and tested according to ASTM D5169-98.

9. The touch fastener loop material of claim 1, having Frazier air permeability of at least 500 $feet^3/feet^2/sec$.

10. The touch fastener loop material of claim 1, having an overall thickness of less than about 1.5 millimeters.

11. The touch fastener loop material of claim 1, wherein the web has an overall basis weight of between 20 gsm and 70 gsm.

12. The touch fastener loop material of claim 1, wherein the fibers comprise multicomponent fibers.

13. The touch fastener loop material of claim 12, wherein the multicomponent fibers comprise bicomponent fibers having a sheath of a lower melting temperature than a core within the sheath, and wherein the fibers are bonded within the base by resin of the sheath.

14. The touch fastener loop material of claim 1, consisting essentially of the non-woven web of fibers, bonded together by fused material of the fibers.

15. The touch fastener loop material of claim 1, wherein the Maximum Fiber Volumetric Ratio occurs within a lower 30 percent of an elevation span between the Rising 5% Ratio Elevation and the Falling 5% Ratio Elevation.

16. A touch fastener comprising the loop material of claim 1 and a backing bonded across a surface of the base opposite the field of loops.

17. The touch fastener of claim 16, wherein the backing is air-impermeable.

18. The touch fastener of claim 16, wherein the loop material and backing are bonded together with an adhesive.

* * * * *